(12) United States Patent
Dunbar et al.

(10) Patent No.: US 11,054,390 B2
(45) Date of Patent: *Jul. 6, 2021

(54) TWO-CHAMBER DUAL-PORE DEVICE

(71) Applicants: The Regents of the University of California, Oakland, CA (US);
Brigham Young University, Provo, UT (US)

(72) Inventors: William Dunbar, Santa Cruz, CA (US);
Holger Schmidt, Santa Cruz, CA (US);
Aaron Hawkins, Provo, UT (US)

(73) Assignees: The Regents of the University of California, Oakland, CA (US);
Brigham Young University, Provo, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/443,025

(22) Filed: Jun. 17, 2019

(65) Prior Publication Data

US 2020/0150084 A1    May 14, 2020

Related U.S. Application Data

(63) Continuation of application No. 15/606,726, filed on May 26, 2017, now abandoned, which is a
(Continued)

(51) Int. Cl.
*G01N 27/327*    (2006.01)
*G01N 27/447*    (2006.01)
(Continued)

(52) U.S. Cl.
CPC ..... *G01N 27/44791* (2013.01); *C12Q 1/6869* (2013.01); *G01N 33/48721* (2013.01); *B82Y 15/00* (2013.01)

(58) Field of Classification Search
CPC .................................................. G01N 33/48721
See application file for complete search history.

(56) References Cited

U.S. PATENT DOCUMENTS 6,627,067 B1 * 9/2003 Branton ............... B24B 37/013
                                                    204/403.06
8,603,303 B2   12/2013 Luan et al.
(Continued)

FOREIGN PATENT DOCUMENTS

WO    2006000064    1/2006
WO    2009030953    3/2009

OTHER PUBLICATIONS

Butler et al. (2008) "Single-molecule DNA detection with an engineered MspA protein nanopore" PNAS, 105(52):20647-20652.
(Continued)

*Primary Examiner* — Alexander S Noguerola
(74) *Attorney, Agent, or Firm* — Brian E. Davy; Bozicevic, Field & Francis LLP

(57) ABSTRACT

Provided is a device comprising a channel through and defined by a plurality of layers surrounding the channel, the channel connecting a first and a second chambers separated by the plurality of layers, wherein the plurality of layers comprise a first layer, a second layer; and a conductive middle layer disposed between the first and second layers, wherein the channel comprises (a) a first region defined by the first layer, denoted as an inlet, that is about 0.5 nm to about 100 nm in diameter and (b) a second region defined by the second layer, denoted as an outlet, wherein the inlet and the outlet are about 10 nm to about 1000 nm apart from each other, and wherein the first and second chambers and the middle layer are connected to a power supply. Also provided are methods of preparing and using the device, in particular for nucleic acid sequencing.

17 Claims, 3 Drawing Sheets

Related U.S. Application Data continuation of application No. 14/358,001, filed as application No. PCT/US2012/064879 on Nov. 13, 2012, now Pat. No. 9,696,277.

(60) Provisional application No. 61/629,184, filed on Nov. 14, 2011.

(51) Int. Cl.
*G01N 33/487* (2006.01)
*C12Q 1/6869* (2018.01)
*B82Y 15/00* (2011.01)

(56) References Cited

U.S. PATENT DOCUMENTS

| | | |
|---|---|---|
| 8,609,826 B2 | 12/2013 | Ueno et al. |
| 9,696,277 B2 | 7/2017 | Dunbar et al. |
| 2005/0014162 A1 | 1/2005 | Barth et al. |
| 2009/0283412 A1 | 11/2009 | Sansinena et al. |

OTHER PUBLICATIONS

Derrington et al. (2010) "Nanopore DNA sequencing with MspA" PNAS, 107(37):16060-16065.
Examination Report No. 1 for Australian Patent Application No. AU 2017202591, dated Jan. 9, 2018, 2pgs.
Office Action for Australian Patent Application No. AU 2012339711, dated Sep. 8, 2014, 2pgs.
Office Action for Australian Patent Application No. AU 2015200179, dated Apr. 16, 2016, 2pgs.
Office Action for Australian Patent Application No. AU 2015200179, dated Aug. 30, 2016, 2pgs.
Office Action for Canadian Patent Application No. CA 2,855,824, dated Sep. 28, 2015, 4pgs.
Office Action for Canadian Patent Application No. CA 2,855,824, dated Nov. 25, 2016, 3pgs.
Office Action for Canadian Patent Application No. CA 2,855,824, dated Oct. 30, 2017, 4pgs.
Office Action for U.S. Appl. No. 14/358,001, dated Sep. 29, 2016, 24pgs.
PCT International Search Report and Written Opinion for PCT/US12/648879, dated Mar. 21, 2013, 5pgs.

* cited by examiner

TWO-CHAMBER DUAL-PORE DEVICE

CROSS REFERENCE TO RELATED APPLICATIONS

This application is a continuation of U.S. application Ser. No. 14/358,001, filed May 13, 2014, which claims the benefit under 35 U.S.C. § 371 of International Patent Application No. PCT/US2012/064879, filed Nov. 13, 2012, which claims the benefit under 35 U.S.C. § 119(e) of U.S. Provisional Application Ser. No. 61/629,184 filed Nov. 14, 2011, entitled "Microfluidic Chip Implementation of Dual-Nanopore Electronics Configuration to Co-Trap Individual DNA Molecules and Methods of Use", the contents of which are incorporated by reference in their entirety into the present disclosure.

BACKGROUND

A nanopore is a nano-scale conduit that forms naturally as a protein channel in a lipid membrane (a biological pore), or is engineered by drilling or etching the opening in a solid-state substrate (a solid-state pore). When such a nanopore is incorporated into a nanodevice comprising two chambers which are separated by the nanopore, a sensitive patch-clamp amplifier can be used to apply a trans-membrane voltage and measure ionic current through the pore.

Nanopores offer great promise for inexpensive whole genome DNA sequencing. In this respect, individual DNA molecules can be captured and driven through the pore by electrophoresis, with each capture event detected as a temporary shift in the ionic current. The sequence of a DNA molecule can then be inferred from patterns within the shifted ionic current record, or from some other auxiliary sensor in or near the nanopore, as DNA passes through the pore channel.

In principle, a nanopore sequencer can eliminate the needs for sample amplification, the use of enzymes and reagents used for catalytic function during the sequencing operation, and optics for detection of sequencing progress, some or all of which are required by the conventional sequencing-by-synthesis methods.

Electric nanopore sensors can be used to detect DNA in concentrations/volumes that are no greater than what is available from a blood or saliva sample. Additionally, nanopores promise to dramatically increase the read-length of sequenced DNA, from 450 bases to greater than 10,000 bases.

There are two principle obstacles to nanopore sequencing: (1) the lack of sensitivity sufficient to accurately determine the identity of each nucleotide in a nucleic acid for de novo sequencing (the lack of single-nucleotide sensitivity), and (2) the ability to regulate the delivery rate of each nucleotide unit through the nanopore during sensing. These two obstacles are often inter-related as the inability to regulate delivery rates is one of the underlying problems can be associated with the lack of single-nucleotide sensitivity. Stated another way, if the DNA is traversing past the sensor too rapidly, then the sensor's function can be compromised. While many research groups are developing and improving nanopores to address obstacle 1, there is no method for addressing obstacle 2 that does not involve the use of enzymes or optics, both of which work only in specialized nanopore techniques and which incur higher complexity and cost compared to purely electrical methods.

SUMMARY

In one embodiment, the present disclosure provides a device, the device comprising a channel through and defined by a plurality of layers surrounding the channel, the channel connecting a first and a second chambers separated by the plurality of layers, wherein the plurality of layers comprise: a first layer; a second layer; and a conductive middle layer disposed between the first and second layers, wherein: the channel comprises (a) a first region defined by the first layer, denoted as an inlet, that is about 0.5 nm to about 100 nm in diameter and (b) a second region defined by the second layer, denoted as an outlet, wherein the inlet and the outlet are about 10 nm to about 1000 nm apart from each other, and wherein the first and second chambers and the middle layer are connected to a power supply.

In one embodiment, the inlet has a depth of from about 0.1 to about 100 nm. In one aspect, wherein the outlet has a diameter greater than the diameter of the inlet. In one aspect, the inlet is about 1 nm to about 20 nm in diameter. In another aspect, the inlet is about 0.2 nm to about 10 nm in depth. In one embodiment, the inlet and outlet are substantially coaxial.

In some aspects, the first layer and/or the second layer comprises a dielectric material. In one aspect, the first layer and/or the second layer comprises a metallic material and wherein the device further comprises insulating material between the first layer and the middle layer and/or between the middle layer and the second layer. In some aspects, the first layer and/or the second layer comprises a material selected from the group consisting of silicon, silicon nitride, silicon dioxide, graphene, carbon nanotubes, $TiO_2$, $HfO_2$, $Al_2O_3$, metallic layers, glass, biological nanopores, membranes with biological pore inserts, and combinations thereof.

In one embodiment, the middle layer comprises a metal selected from chrome, aluminum, platinum, and gold. In another alternative embodiment, the middle layer comprises a metal that can be deposited with thin film methods such as e-beam evaporation, thermal evaporation, molecular beam epitaxi (MBE), or atomic layer deposition (ALD).

The device, in one embodiment, can further comprise the power supply wherein the power supply is configured to provide a first voltage between the first chamber and the middle layer, and a second voltage between the middle layer and the second chamber, and wherein the first voltage and the second voltage are independently adjustable. In one aspect, the power supply comprises a voltage-clamp system or a patch-clamp system to generate each of the first and second voltages. In one aspect, the middle layer is adjusted to be ground relative to the two voltages.

In some aspects, the device further comprises at least one sensor capable of identifying a polymer or individual components of a polymer during movement of the polymer through the inlet and outlet. In one aspect, the sensor measures an ionic current across the inlet.

In one aspect, the sensor is configured to identify the polymer or the individual components by measuring a current, a voltage, pH, an optical feature, or residence time associated with the polymer or one or more components of the polymer.

In one aspect, the sensor is configured to form a tunnel gap allowing the polymer to pass through the tunnel gap when the polymer is loaded within the inlet and outlet.

It is contemplated that the plurality of layers can be continuous regions of an integrated piece, or alternatively the plurality of layers are discontinuous.

Also provided, in one embodiment, is a method for controlling the movement of a charged polymer through a pore, comprising: (a) loading a sample comprising a charged polymer in one of the first or second chamber of the device, wherein the device is connected to a voltage-clamp or patch-clamp system for providing a first voltage between the first chamber and the middle layer, and a second voltage between the middle layer and the second chamber; (b) setting an initial first voltage and an initial second voltage so that the polymer moves through the chambers, thereby locating the polymer across both the inlet and outlet; and (c) adjusting the first voltage and the second voltage so that both voltages generate force to pull the charged polymer away from the middle layer, wherein the two voltages are different in magnitude, under controlled conditions, so that the charged polymer moves through the channel and both the inlet and the outlet in one direction and in a controlled manner.

In one aspect, the charged polymer is a polynucleotide. In another alternative aspect the charged polymer is a polypeptide. Other charged polymers provided by the invention include phospholipids, polysaccharides, and polyketides In one aspect, the adjusted first voltage and second voltage at step (c) are about 10 times to about 10,000 times as high, in magnitude, as the difference between the two voltages.

Still further provided, in one aspect, is a method for preparing a device of the present disclosure, comprising drilling a channel through a plurality of layers comprising a first layer, a second layer and a conductive middle layer disposed between and insulated from the first and second layers. In some aspects, the method further includes shrinking one or more of the plurality of layers to reduce the diameter and/or depth of the inlet and/or the outlet. In some aspects, the drilling is carried out by focused ion beam.

In another exemplary embodiment, the device comprises a nanopore input head, comprising: a first nanopore having a first pore opening and enclosing a first ionic conductor; a second nanopore having a second pore opening and enclosing a second ionic conductor; a nanopore chamber between said first nanopore and said second nanopore, said nanopore chamber enclosing an chamber ionic conductor that is biased substantially at electrical ground, said nanopore chamber having body having a first aperture aligned with said first pore opening and a second aperture aligned with said second pore opening; a first differential amplifier having a first non-inverting input operatively connected to said first ionic conductor, a first inverting input, and a first output; and a second differential amplifier having a second non-inverting input operatively connected to said second ionic conductor, a second inverting input, and a second output; wherein a width of said nanopore chamber is less than 1 micron (μm).

The invention also discloses a method of capturing a strand of DNA comprising the steps of: disposing first and second nanopore sensors within 1 micron of each other and within an ionic chamber; electrically grounding said ionic chamber to electrically isolate the first and second nanopore sensors; applying a first voltage to the first nanopore sensor to capture part of a strand of DNA; and applying a second voltage to the second nanopore sensor to capture another part of the strand of DNA.

The invention further discloses a nanopore system, comprising the solid-state nanopore systems and associated circuits disclosed here.

The nanopore device systems may comprise cis and trans chambers connected by an electrical communication means. In one embodiment the chambers comprise a medium, the medium selected from the group consisting of an aqueous medium, a non-aqueous medium, an organic medium, or the like. In one embodiment the medium is a fluid. In an alternative embodiment the medium is a gas. In one embodiment the electrical communication means is a solid state pore comprising, for example, silicon nitride, bifunctional alkyl sulfide, and/or gold or other metal or alloy. In the alternative, the cis and trans chambers are separated by a thin film comprising at least one pore or channel. In one preferred embodiment, the thin film comprises a compound having a hydrophobic domain and a hydrophilic domain. In a more preferred embodiment, the thin film comprises a phospholipid. The devices further comprise a means for applying an electric field between the cis and the trans chambers. In one embodiment the pore or channel accommodates a part of the polyion. In another embodiment the pore or channel accommodates a part of the molecule. In one preferred embodiment, the molecule is a macromolecule. In another preferred embodiment the polyion is selected from the group consisting of polynucleotides, polypeptides, phospholipids, polysaccharides, and polyketides.

In one embodiment the compound comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, ribozyme, and the like. In a more preferred embodiment the enzyme activity can be enzyme activity of DNA polymerase, RNA polymerase, endonuclease, exonuclease, DNA ligase, DNase, uracil-DNA glycosidase, kinase, phosphatase, methylase, acetylase, glucose oxidase, ribozyme, and the like.

In another embodiment the pore is sized and shaped to allow passage of an activator, wherein the activator is selected from the group consisting of ATP, $NAD^+$, $NADP^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, S-adenosylmethionine, hexose sugars, pentose sugars, phospholipids, lipids, glycosyl phosphatidyl inositols (GPIs), and any other biological activator.

In another embodiment the pore is sized and shaped to allow passage of a monomer, wherein the monomer is selected from the group consisting of dATP, dGTP, dCTP, dTTP, UTP, alanine, cysteine, aspartic acid, glutamic acid, phenylalanine, glycine, histidine, isoleucine, lysine, leucine, methionine, asparagines, proline, glutamine, arginine, serine, threonine, valine, tryptophan, tyrosine, hexose sugars, pentose sugars, phospholipids, lipds, and any other biological monomer.

In yet another embodiment the pore is sized and shaped to allow passage of a cofactor, wherein the cofactor is selected from the group consisting of $Mg^{2+}$, $Mn^{2+}$, $Ca^{2+}$, ATP, $NAD^+$, $NADP^+$, and any other biological cofactor.

In one preferred embodiment, the dual-nanopore system comprises a solid-state nanopore comprising, for example, a layer of graphene or other similar composition.

In an alternative embodiment the pore or channel comprises a biological molecule, or a synthetic modified or altered biological molecule. Such biological molecules are, for example, but not limited to, an ion channel, such as α-hemolysin, a nucleoside channel, a peptide channel, a sugar transporter, a synaptic channel, a transmembrane receptor, such as GPCRs, a receptor tyrosine kinase, and the like, a T-cell receptor, an MHC receptor, a nuclear receptor, such as a steroid hormone receptor, a nuclear pore, or the like.

In an alternative, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycosyl phosphatidyl inositols, glycophosphoinositols, lipopolysaccharides, or the like. The compound can have antigenic activity. The compound can have ribozyme activity. The compound can have selective binding properties whereby the polymer binds to the compound under a particular controlled environmental condition, but not when the environmental conditions are changed. Such conditions can be, for example, but not limited to, change in [H⁺], change in environmental temperature, change in stringency, change in hydrophobicity, change in hydrophilicity, or the like.

In one embodiment the macromolecule comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, kinase, phosphatase, methylase, acetylase, glucose oxidase, or the like. In an alternative embodiment, the macromolecule can comprise more that one enzyme activity, for example, the enzyme activity of a cytochrome P450 enzyme. In another alternative embodiment, the macromolecule can comprise more than one type of enzyme activity, for example, mammalian fatty acid synthase. In another embodiment the macromolecule comprises ribozyme activity.

In an alternative, the macromolecule comprises non-enzyme biological activity. The macromolecule having non-enzyme biological activity can be, for example, but not limited to, proteins, peptides, antibodies, antigens, nucleic acids, peptide nucleic acids (PNAs), locked nucleic acids (LNAs), morpholinos, sugars, phospholipids, lipids, glycosyl phosphatidyl inositols, glycophosphoinositols, lipopolysaccharides, or the like. The macromolecule can have polynucleotide-binding activity and/or polypeptide biosynthesis activity, such as, but not limited to, a ribosome or a nucleosome. The macromolecule can have antigenic activity. The macromolecule can have selective binding properties whereby the polymer binds to the macromolecule under a particular controlled environmental condition, but not when the environmental conditions are changed. Such conditions can be, for example, but not limited to, change in [H⁺], change in environmental temperature, change in stringency, change in hydrophobicity, change in hydrophilicity, or the like.

In another embodiment, the invention provides a compound, wherein the compound further comprises a linker molecule, the linker molecule selected from the group consisting of a thiol group, a sulfide group, a phosphate group, a sulfate group, a cyano group, a piperidine group, an Fmoc group, and a Boc group. In another embodiment the compound is selected from the group consisting of a bifunctional alkyl sulfide and gold.

BRIEF DESCRIPTION OF THE DRAWINGS

Provided as embodiments of this disclosure are drawings which illustrate by exemplification only, and not limitation, wherein.

Figure 1:
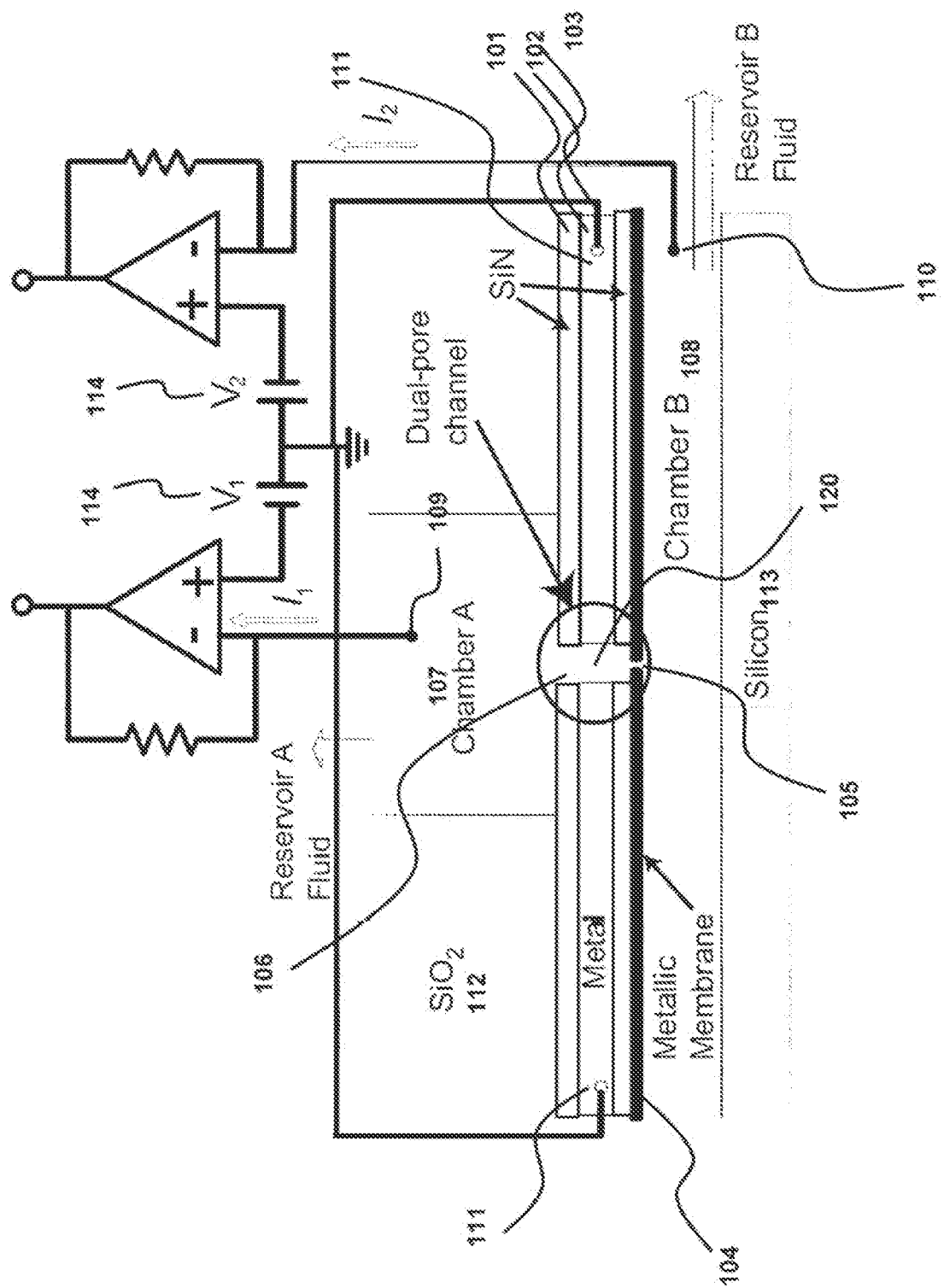
FIG. 1 shows schematic of a two-chamber dual-pore device along with a dual-amplifier electronics layout for independent voltage control ($V_1$, $V_2$) and current measurement ($I_1$, $I_2$) of each pore. Chambers A and B are volumetrically separated except through the dual-pore channel, comprised of a ~30 nm diameter channel drilled through SiN-metal-SiN layers, and a metallic membrane with a 2-10 nm nanopore.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used in the specification and claims, the singular form "a", "an" and "the" include plural references unless the context clearly dictates otherwise. For example, the term "an electrode" includes a plurality of electrodes, including mixtures thereof.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this invention.

All numerical designations, for example, distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary and that equivalents of such are known in the art.

Device for Detecting Polymers

One embodiment of the present disclosure provides a device that includes a channel through and defined by a plurality of layers surrounding the channel, the channel connecting a first and a second chambers separated by the plurality of layers. Accordingly, the channel enables fluid communication between the chambers. Further, the channel is comprised of regions that are defined by the layers surrounding these regions.

In one aspect, the plurality of layers include at least a first layer, a second layer, and a conductive middle layer disposed between the first and second layers. The region defined by the first layer is denoted as an inlet (or alternatively a "first pore") and the region defined by the second layer is denoted as an outlet (or alternatively as a "second pore"). It is noted that the terms inlet and outlet are relative terms and thus do not require that, for instance, fluid must enter the inlet and come out of the outlet. Collectively, such a device is also termed a "two-chamber dual-pore device."

In one aspect, the first and second chambers and the middle layer are connected to a power supply. As such, voltages can be established between the first chamber and the middle layer and between the middle layer and the second chamber. In some aspects, these two voltages are independently adjustable.

FIG. 1 illustrates such a device, which includes a channel 120 surrounded by a number of layers including a first layer (104), a second layer (101) and a middle layer (102) between the first and second layer. In this example, an additional layer (103) is provided between the first layer and the middle layer, which is made of the same material as the second layer 101. Here, the second layer 101 and layer 103 are both made of silicon whereas the middle layer 102 is metal. The first layer 104 is a metallic membrane. As the layer 103 is not conductive, the first layer 104 and the middle layer 102 insulated from each other.

The channel 120 can be considered to be comprised of multiple regions, each region defined by the surrounding layer. In this context, the portion of the channel defined by the first layer 104 can be denoted as an inlet (105), and the portion of the channel defined by the second layer 101 can be denoted as an outlet (106).

The device in FIG. 1 further includes two chambers, 107 ("Chamber A") and 108 ("Chamber B"), which have fluid communication through the channel 120 only. The chambers can be formed with walls (for example, 112 and 113) that are comprised of materials such as silicon.

Diameters, depths and distance of the inlet and outlet of the device can be adjusted for particular use of the device. For instance, in one aspect, the inlet has a diameter that is about 0.5 nm to about 100 nm. In another aspect, the diameter is at least about 0.5, or 1, 2, 3, 4, 5, 10, 15, 20, 25, 30, 40 or 50 nm. In another aspect, the diameter is not greater than about 100, or 90, 80, 70, 60, 50, 40, 35, 30, 25, 20, 15, or 10 nm. In one aspect, the inlet is about 1 nm to about 20 nm in diameter.

In one aspect, the outlet has a diameter that is about 0.5 nm to about 100 nm. In another aspect, the diameter of the outlet is at least about 0.5, or 1, 2, 3, 4, 5, 10, 15, 20, 25, 30, 40 or 50 nm. In another aspect, the diameter is not greater than about 100, or 90, 80, 70, 60, 50, 40, 35, 30, 25, 20, 15, or 10 nm. In one aspect, the outlet is about 1 nm to about 20 nm in diameter. In some aspects, the outlet's diameter is greater than that of the inlet.

In one aspect, the inlet has a depth that is from about 0.1 nm to about 100 nm. In one aspect, the depth of the inlet is at least about 0.1 or 0.2, 0.3, 0.4, 0.5, 0.6, 0.7, 0.8, 0.9, 1, 1.5, 2, 3, 4, 5, 10, 15 or 20 nm. In another aspect, the depth is not greater than about 100, or 90, 80, 70, 60, 50, 40, 35, 30, 25, 20, 15, or 10 nm. In one aspect, the inlet is about 0.2 nm to about 10 nm in depth.

In one aspect, the outlet has a depth that is from about 0.1 nm to about 100 nm. In one aspect, the depth of the outlet is at least about 0.1 or 0.2, 0.3, 0.4, 0.5, 0.6, 0.7, 0.8, 0.9, 1, 1.5, 2, 3, 4, 5, 10, 15 or 20 nm. In another aspect, the depth is not greater than about 100, or 90, 80, 70, 60, 50, 40, 35, 30, 25, 20, 15, or 10 nm. In one aspect, the outlet is about 0.2 nm to about 10 nm in depth.

In some aspects, the inlet and the outlet are about 10 nm to about 1000 nm apart from each other. Such a distance, in one aspect, is at least about 10, or 20, 30, 40, 50, 60, 70, 80, 90 or 100 nm and, in another aspect, is not greater than about 1000, or 900, 800, 700, 600, 500, 400, 300, 200 or 100 nm.

In some aspects, the inlet has a substantially round shape. "Substantially round", as used here, refers to a shape that is at least about 80 or 90% in the form of a cylinder. In some embodiments, the pore is square, rectangular, triangular, oval, or hexagonal in shape.

It is shown that each of the two chambers and the middle layer of the device is connected to a power supply. The power supply 114, as shown, is connected to the middle layer 102 at electrode 111, to Chamber A at electrode 109 and to Chamber B at electrode 110. In one aspect, the middle layer is grounded, and the voltages rendered between the middle layer and each of the two chambers is independently adjustable.

Figure 2:
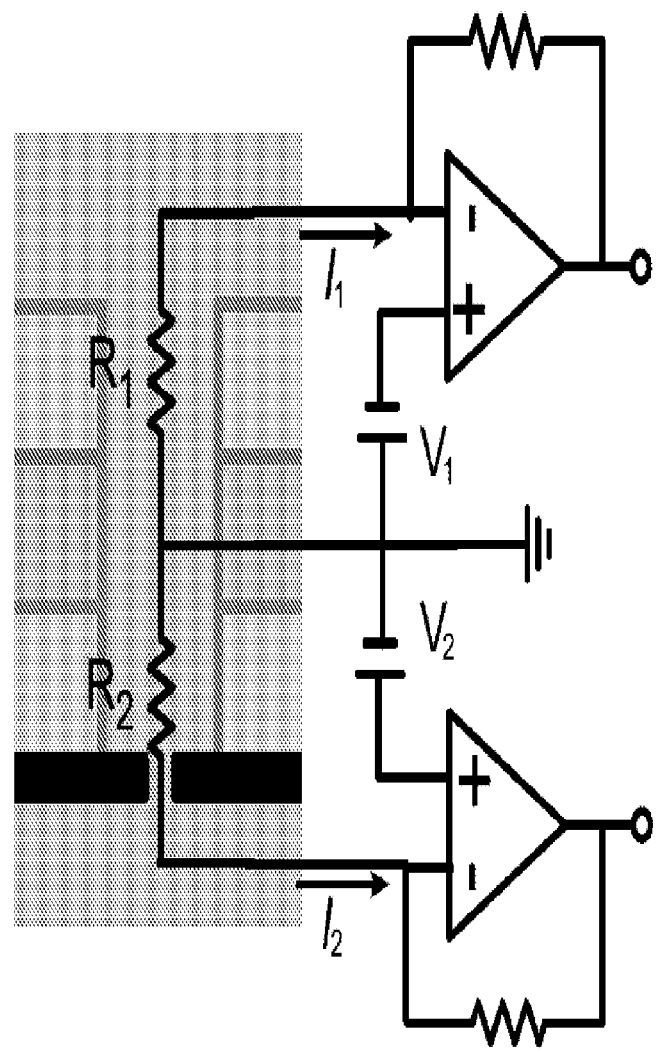
FIG. 2 shows that, electrically, $V_1$ drops across resistance $R_1$ associated with resistance of the ~30 nm channel path through top SiN membrane, and $V_2$ drops across $R_2$ which is dominated by the resistance of the smaller nanopore in the metallic membrane. Shrinking the top pore can increase $R_1$ until $R_1 \approx R_2$. The metal layer (a continuous sheet of chrome or silver for example) will serve as a grounded electrode surface in the channel.

An exemplary setup for generation and adjustment of the voltages is provided in FIG. 2. Electrically, $V_1$ drops across resistance $R_1$ (between Chamber A and the middle layer) associated with resistance of the ~30 nm channel path through top SiN membrane, and $V_2$ drops across $R_2$ (between Chamber B and the middle layer) which is dominated by the resistance of the inlet, which in this case has a smaller diameter than the outlet.

In some aspects, the power supply is comprised of a voltage-clamp or a patch-clamp for supplying the voltage across each pore, which can also measure the current through each pore independently. In this respect, the power supply can set the middle layer to a common ground for both voltage sources. In one aspect, the power supply is configured to provide a first voltage between one chamber (for example, Chamber A in FIG. 1) and the middle layer, and a second voltage between the second chamber (for example, Chamber B in FIG. 1) and the middle layer.

Adjustment of the voltages can be used to control the movement of charged particles in the channel. For instance, when both voltages are set in the same direction, a properly charged particle can be moved from the one chamber to the middle of the channel and to the other chamber, or the other way around, sequentially. Otherwise, a charged particle can be moved from either of the chambers to the middle of the channel and kept there.

The adjustment of the voltages in the device can be particularly useful for controlling the movement of a large molecule, such as a charged polymer, that is long enough to cross the entire channel at the same time. In such an aspect, the movement and the rate of movement of the molecule can be controlled by the relative magnitude and direction of the voltages, which will be further described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. A single sheet of graphene forms a membrane ~0.3 nm thick, and can be used as the pore-bearing membrane, for example.

Fabrication of the Device

The present disclosure, in one embodiment, provides an integrated two-chamber dual-pore device, which can be smaller than the size of a desktop PC, and will enable long-read (>10 kbp) nanopore sequencing. In one aspect, the device is based on the dual-pore configuration that incorporates a pair of vertically-aligned pores drilled in parallel substrates, with each pore independently controlled using a dual amplifier architecture (FIG. 1). Such a device leverages an integrated amplifier and microfluidic devices incorporating solid-state nanopores.

It is contemplated that such a design can reduce and control the rate of DNA passage through the nanopores, while still generating a sequence-sensitive current.

Chip fabrication and nanopore fabrication can be done using thin film deposition and etching along with focused ion beam (FIB) milling. Electron beams can also be used, in addition to ion beams, to drill nanopores and channels. A silicon substrate can serve as a template and thin films of metal and dielectric material ($SiO_2$ and silicon nitride) can be deposited using evaporation and chemical vapor deposition. Metallic materials include chrome (Cr), aluminum (Al), platinum (Pt), gold (Au), or any other metal that can be deposited with contemporary thin film deposition methods such as e-beam evaporation, thermal evaporation, MBE (molecular beam epitaxy), or ALD (atomic layer deposition).

Photolithography and chemical etching can be used to form hollow spaces for fluid entry and electrical access to metallic layers. A micropore (4 µm diameter) can first be opened through reactive etching and then an initial nanopore (~30 nm diameter) can be drilled using an FIB. This process can be successfully been used to define nanopores in ~100 nm thin dielectric membranes.

Active feedback can allow the drilling of a second, smaller nanopore (2-10 nm) in a thin metallic layer, forming the most significant sensing aperture (see FIG. 1). Both nanopores can be sculpted (shrunk) to the desired size individually by applying the correct beam focus to each layer (FIG. 3), and this method can be used for improved sensing and control. Having both pores 2-10 nm can facilitate detangling of long ssDNA, for example, or enable cross-correlation of the recorded ionic currents (pores of common diameters have comparable signal-to-noise ratios).

The 10 nm metallic membrane can be refined for single-nucleotide sensitivity by thinning the membrane near the site of nanopore drilling. FIB-sculpting the membrane near the pore can achieve 1-2 nm thickness, followed by FIB-drilling the pore to 2-5 nm diameter. Direct sequencing of long (>10 kbp) single-stranded DNA can be attempted. The ssDNA will form a large amount of secondary structure, which must be unravelled for nanopore sensing and control. It has been shown that this is achievable, using a single 8 nm nanopore in a Si-membrane.

As an alternative to the metallic membrane, one can incorporate a graphene layer into the chip. Incorporating graphene will be more complex process, but the membrane is durable and likely to provide single-nucleotide sensitivity. In particular, graphene has been shown to function as an insulating membrane, and with a drilled nanopore, capable of detecting capture and passage of DNA. Researchers have shown that drilling nanopores in multi-layered graphene membranes results in a terrace effect, enabling the use of thicker and thus sturdier membranes that are thin near the pore. Numerical studies also support that ionic current through a 2.5 nm graphene pore would be single-nucleotide sensitive (Venkatesan and Bashir, *Nature Nanotechnology*, 6:615-624, 2011), but no experiment has shown this due (in part) to the lack of a DNA rate control method that is graphene compatible.

Controlling Movement of Molecules with the Device

By virtue of the voltages present at the inlet and outlet of the device, charged molecules can be moved through the pores between chambers. Speed and direction of the movement can be controlled by the magnitude and direction of the voltages. Further, because each of the two voltages can be independently adjusted, the movement and speed of a charged molecule can be finely controlled in each chamber and through the channel.

One example concerns a charged polymer, such as a polynucleotide, having a length that is longer than the distance between the two pores. For example, a 1000 bp dsDNA is ~340 nm in length, and would be substantially longer than a channel that include an inlet and an outlet, each being 10 nm in depth and 100 nm apart. In a first step, the polynucleotide is loaded into either of the two chambers. By virtue of its negative charge under a physiological condition (~pH 7.4), the polynucleotide can be moved across the channel. Therefore, in a second step, two voltages, in the same direction and at the same or similar magnitudes, are applied to the channel to induce movement of the polynucleotide across both the inlet and the outlet sequentially.

At about time when the polynucleotide reaches the end of the channel, one or both of the voltages can be changed. Since the distance between the inlet and the outlet is selected to be shorter than the length of the polynucleotide, when the polynucleotide reaches the end of the channel, it spans the entire channel. A prompt change of direction of the voltage at the first pore, therefore, will generate a force that pulls the polynucleotide straight, across the channel (illustration in FIG. 3).

If, at this point, the magnitude of the voltage-induced force at one side is less than that of the voltage-induced force at the other side of the channel, then the polynucleotide will continue crossing the channel, but at a lower speed. In this respect, it is readily appreciated that the speed and direction of the movement of the polynucleotide can be controlled by the directions and magnitudes of both voltages. As will be further described below, such a fine control of movement has broad applications.

Accordingly, in one aspect, provided is a method for controlling the movement of a charged polymer through a channel. The method entails (a) loading a sample comprising a charged polymer in one of the first or second chamber of the device of any of the above embodiments, wherein the device is connected to a voltage-clamp or patch-clamp system for providing a first voltage between the first chamber and the middle layer, and a second voltage between the middle layer and the second chamber; (b) setting an initial first voltage and an initial second voltage so that the polymer moves through the chambers, thereby locating the polymer across both the inlet and outlet; and (c) adjusting the first voltage and the second voltage so that both voltages generate force to pull the charged polymer away from the middle layer (voltage-competition mode), wherein the two voltages are different in magnitude, under controlled conditions, so that the charged polymer moves through the channel and both the inlet and the outlet in one direction and in a controlled manner.

For the purpose of establishing the voltage-competition mode in step (c), the relative force exerted by each voltage at each pore is to be determined for each two-pore device used, and this can be done with calibration experiments by observing the influence of different voltage values on the motion of the polynucleotide (motion can be measured by sensing location-known and detectable features in the polynucleotide, with examples of such features detailed later in this document). If the forces are equivalent at each common voltage, for example, then using the same voltage value at each of the inlet and outlet (with common polarity in both chambers relative to grounded middle layer) creates a zero net motion in the absence of thermal agitation (the presence and influence of Brownian motion is discussed below). If the forces are not equivalent at each common voltage, then achieving equal forcing requires identification and use of a larger voltage at the inlet or outlet that experiences a weaker force at the common voltage. Calibration for voltage-competition mode is required for each two-pore device, and would be required for specific charged polymers or molecules for which features that pass through each pore influence the force.

In one aspect, the sample containing the charged polymer is loaded into the first chamber and the initial first voltage is set to pull the charged polymer from the first chamber to the middle of the channel and the initial second voltage is set to pull the polymer from the middle of the channel to the second chamber. Likewise, the sample can be initially loaded into the lower chamber.

In another aspect, the sample containing the charged polymer is loaded into the channel and the initial first voltage is set to pull the charged polymer from the channel to the first chamber and the initial second voltage is set to pull the charged polymer from the channel to the second chamber.

The term "charged polymer" or "polymer" refers to a polymer that contains sufficient charged units at the pH of the solution that it can be pulled through a pore by electrostatic forces. In one embodiment, each unit of the charged polymer is charged at the pH selected. In another embodiment, the charged polymer is comprised of sufficient charged units to be pulled into and through the pores by electrostatic forces. For example, a peptide containing sufficient entities which can be charged at a selected pH (lysine, aspartic acid, glutamic acid, etc.) so as to be used in the devices and methods described herein is a charged polymer for purposes of this invention. Likewise, a copolymer comprising methacrylic acid and ethylene is a charged polymer for the purposes of this invention if there is sufficient charged carboxylate groups of the methacrylic acid residue to be used in the devices and methods described herein is a charged polymer for purposes of this invention. In one embodiment, the charged polymer is comprised one or more charged units at or close to one terminus of the polymer. In another embodiment, the charged polymer is comprised of one or more charged units at or close to both termini of the polymer.

In some aspects, the charged polymer is a polynucleotide or a polypeptide. In a particular aspect, the charged polymer is a polynucleotide. Non-limiting examples of polynucleotides include double-stranded DNA, single-stranded DNA, double-stranded RNA, single-stranded RNA, and DNA-RNA hybrids.

In one aspect, the adjusted first voltage and second voltage at step (c) are about 10 times to about 10,000 times as high, in magnitude, as the difference between the two voltages. For instance, the two voltages are 90 mV and 100 mV, respectively. The magnitude of the voltages (~100 mV) is about 10 times of the difference between them, 10 mV. In some aspects, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 7000 times, 8000 times or 9000 times as high as the difference between them. In some aspects, the magnitude of the voltages is no more than about 10000 times, 9000 times, 8000 times, 7000 times, 6000 times, 5000 times, 4000 times, 3000 times, 2000 times, 1000 times, 500 times, 400 times, 300 times, 200 times, or 100 times as high as the difference between them.

In one aspect, real-time or on-line adjustments to first voltage and second voltage at step (c) are performed by active control or feedback control using dedicated hardware and software, at clock rates up to hundreds of megahertz. Automated control of the first or second or both voltages is based on feedback of the first or second or both ionic current measurements.

Sensor in the Device

The device of the present disclosure can be used to carry out analysis of molecules or particles that move or are kept within the device. In one aspect, the device further includes one or more sensors to carry out the analysis. In one aspect, the sensor includes a pair of electrodes placed at two sides of the inlet or the outlet to measure an ionic current across the inlet or the outlet when a molecule or particle, in particular a polymer, moves through.

In an alternative aspect, when a single sensor in used, it is contemplated that the single sensor preferably does not include such a pair of ionic current sensors. In one aspect, the device includes a sensor suitable for identifying a polymer, or individual components of a polymer. Non-limiting examples of individual components include monomer units and monomer units with modifications approximate to or on the monomer unit. When the polymer is a polynucleotide, an individual component can be one or more nucleotide units or the nucleotide units bound by a protein factor, without limitation.

The sensors used in the device can be any sensor suitable for identifying a molecule or particle, such as a polymer. For instance, a sensor can be configured to identify the polymer by measuring a current, a voltage, pH, an optical feature or residence time associated with the polymer or one or more individual components of the polymer.

In one embodiment, the sensor measures an optical feature of the polymer or a component (or unit) of the polymer. One example of such measurement includes identification by infrared (or ultraviolet) spectroscopy of an absorption band unique to a particular unit.

When residence time measurements are used, they will correlate the size of the unit to the specific unit based on the length of time it takes to pass through the sensing device.

Still further, the sensor can include an enzyme distal to that sensor which enzyme is capable of separating the terminal unit of the polymer from the penultimate unit thereby providing for a single molecular unit of the polymer. The single molecule, such as a single nucleotide or an amino acid, can then be detected with methods such as mass spectrometry. Methods for measuring such a single unit are known in the art and include those developed by Caltech (see, for example, http://spectrum.ieee.org/tech-talk/at-work/test-and-measurement/a-scale-for-weighing-single-molecules). The results of that analysis can be compared to those of the sensing device to provide confirmation of the correct analysis.

Accordingly, the sensor can be placed at a location within the device that enables such measurement. In one aspect, the sensor can include two electrodes and be placed in either or both the inlet and outlet. When the polymer moves across the channel, the two electrodes are then on both sides of the polymer and thus can identify an individual component by measuring a current or a voltage, or the change thereof, across the individual component.

In yet another aspect, the sensor does not include electrodes but takes a form of a membrane or scaffold having an opening (for example, a hole) that allows passing of a polymer. For instance, one or more layers of graphene membrane with an opening, which can be just like a nanopore as the other nanopores, can act as the auxiliary sensor, which itself is positioned in the chamber between the inlet and outlet. In one aspect, the graphene member comprises a single sheet, double sheet, or more than two sheets.

In some embodiments, the sensor is configured to proximate a polymer when the polymer is loaded in both the first and the second pores. Therefore, when the polymer moves through the channel, the sensor is close enough to the polymer to measure the polymer.

In some embodiments, the sensor is configured to form a tunnel gap allowing a polymer to pass through the tunnel gap. When a polymer moves through the tunnel gap, the sensor is then able to identify the individual components of the polymer. It has been shown that individual nucleotides can be discriminated in a precision 0.8 nm tunneling gap.

In some embodiments, the sensor is functionalized with reagents that form distinct non-covalent bonds with each DNA base. In this respect, the gap can be larger and still allow effective measuring. For instance, a 2.5 nm gap can be as effective, when used with a functionalized, as a 0.8 nm gap. Tunnel sensing with a functionalized sensor is termed "recognition tunneling." Using a Scanning Tunneling Microscope (STM) with recognition tunneling, a DNA base flanked by other bases in a short DNA oligomer can be identified.

Recognition tunneling can also provide a "universal reader" designed to hydrogen-bond in a unique orientation to each of the four DNA bases (A, C, G, T) and also to the base 5-methyl-cytosine (mC) which is naturally occurring due to epigenetic modifications.

A limitation with the conventional recognition tunneling is that it can detect only freely diffusing DNA that randomly binds in the gap, or that happens to be in the gap during microscope motion, with no method of explicit capture to the gap. Further, the collective drawbacks of the STM setup will go away when the recognition reagent, once optimized for sensitivity, is incorporated within an electrode tunneling gap in a nanopore channel.

Accordingly, in one embodiment, the sensor comprises surface modification by a reagent. In one aspect, the reagent is capable of forming a non-covalent bond with a nucleotide. In a particular aspect, the bond is a hydrogen bond. Non-limiting examples of the reagent include 4-mercaptobenzamide and 1-H-Imidazole-2-carboxamide.

A significant advantage of the methods in the present technology is that is that they can be engineered, in principle, to provide direct tracking of progress through homopolymeric regions (base repeats). Direct base repeat tracking is not possible with ionic current sensing. Tracking repeats is essential, for example, since deletions and insertions of specific mononucleotide repeats (7, 9 nt) within human mitochondrial DNA have been implicated in several types of cancer.

In ionic current sensing, there is no distinct signal-per-nucleotide of motion of homopolymeric ssDNA through the pore. It is contemplated that an ideal nanopore sequencing platform should utilize an auxiliary sensing method that can track per-nucleotide motion progress while also achieving single-nucleotide sensitivity. Transitions between neighboring nucleotides in oligomers can be observable with recognition tunneling, making it a candidate for sequencing that permits direct base-repeat tracking.

Therefore, the methods of the present technology can provide DNA delivery rate control for one or more recognition tunneling sites, each positioned in one or both of the nanopore channels, and voltage control can ensure that each nucleotide resides in each site for a sufficient duration for robust identification.

Sensors in the devices and methods of the present disclosure can comprise gold, platinum, graphene, or carbon, or other suitable materials. In a particular aspect, the sensor includes parts made of graphene. Graphene can act as a conductor and an insulator, thus tunneling currents through the graphene and across the nanopore can sequence the translocating DNA.

In some embodiments, the tunnel gap has a width that is from about 1 nm to about 20 nm. In one aspect, the width of the gap is at least about 1 nm, or alternatively at least about 1.5, 2, 2.5, 3, 3.5, 4, 4.5, 5, 6, 7, 8, 9, 10, 12 or 15 nm. In another aspect, the width of the gap is not greater than about 20 nm, or alternatively not greater than about 19, 18, 17, 16, 15, 14, 13, 12, 11, 10, 9, 8, 7, 6, 5, 4, 3, or 2 nm. In some aspects, the width is between about 1 nm and about 15 nm, between about 1 nm and about 10 nm, between about 2 nm and about 10 nm, between about 2.5 nm and about 10 nm, or between about 2.5 nm and about 5 nm.

Characterization of a Polymer in the Device

A polymer, such as a DNA molecule, can be analyzed in the device of the present disclosure. In one aspect, the polymer is loaded into the channel in the device, as described above. Once the polymer is loaded, it is at a position suitable for detection by the sensor, by means of measuring a current, a voltage, pH, an optical feature or residence time associated with the polymer or components of the polymer.

For instance, a polynucleotide can be loaded into the channel by two voltages having the same direction. In this example, once the direction of the voltage applied at the first pore (either of the inlet or outlet) is inversed and the new voltage-induced force is slightly less, in magnitude, than the voltage-induced force applied at the second pore (the other of the inlet or outlet), the polynucleotide will continue moving in the same direction, but at a markedly lower speed.

In this respect, the amplifier supplying voltage across the second pore also measures current passing through the second pore, and the sensor then determines the identification of a nucleotide that is passing through the pore, as the passing of each different nucleotide would give rise to a different current signature (for example, based on shifts in the ionic current amplitude). Identification of each nucleotide in the polynucleotide, accordingly, reveals the sequence of the polynucleotide.

In some aspects, repeated controlled delivery for re-sequencing a polynucleotide further improves the quality of sequencing. Each voltage is alternated as being larger, for controlled delivery in each direction. Also contemplated is that the two currents through the two pores can be correlated to improved accuracy. It is contemplated that Brownian motion may cause fluctuations in the motion of a molecule, affecting controlled delivery of the molecule. Such an effect, however, can be minimized or avoided by, for example, during DNA sequencing, repeated controlled delivery of the DNA and averaging the sequencing measurements. Still further, it is contemplated that the impact of Brownian motion on the controlled motion of large molecules, such as polynucleotides and polypeptides, would be insignificant in particular when competing forces are pulling the largest molecules apart, generating tension within the molecule. It is contemplated that adhesion of the DNA to the pore walls, by surface charge modifications or chemistry to the pore surface, to create friction can also mitigate the influence of Brownian motion on the control performance of the two pore method.

Such a method provides a ready solution to problems that have not been solved in the prior art.

For instance, it is known that there are two competing obstacles to achieve the controlled delivery and accurate sensing required for nanopore sequencing. One is that a relatively high voltage is required, at the pore, to provide enough sequencing sensitivity. On the other hand, high voltages lead to fast passing of a polynucleotide through the pore, not allowing sufficient time for identification of each nucleotide.

More specifically, the nanopore sequencing platform requires that the rate of polynucleotide passage through the pore be controlled to 1 ms/nucleotide (nt) or slower, while still generating a sequence-sensitive current. This requires sufficiently high signal-to-noise for detecting current signatures (high voltage is better), but sufficiently slow motion of the molecule through the pore to ensure measurements are within the recording bandwidth (low voltage is better). In single pore implementations, polynucleotide speed is proportional to voltage, so higher voltage is better for sensing but worse for reducing polynucleotide speed: rates are 1 µs/nt and faster (>1000 times too fast) at voltages that promote polynucleotide capture. On the other hand, lower voltages reduce sensing performance, and also increase the relative contribution of rate fluctuations caused by Brownian motion that will undermine read accuracy.

Other than what is described herein, there are currently no methods for addressing these obstacles that do not involve the use of enzymes or optics, both of which work only in specialized nanopore techniques.

Several approaches have been proposed to address the problem associated with the lack of sensing capability, and under low voltages. One is to engineer biological nanopores to improve their sensitivity. Another is to use graphene membranes, which as a single sheet are thinner than the distance between nucleotides in ssDNA. Still another is the use of an auxiliary current measured in close proximity to the nanopore (for example, tunneling currents).

Biological nanopores have been tested in the first approach. The α-hemolysin nanopore is the most commonly used biological pore in research. Studies have shown that α-hemolysin can resolve single nucleotide substitutions in homopolymers and abasic (1',2'-dideoxy) residues within otherwise all-nucleobase DNA. However, single nucleotide sensitivity is not possible in heteromeric DNA with wild-type (WT) α-hemolysin, for which the ionic current is influenced by ~10 nucleotides in the channel. Protein engineering of α-hemolysin has been used to improve its sensitivity for DNA analysis and sequencing. One such mutant pore uses α-hemolysin with a covalently attached molecular adapter (Clarke et al., Nat. Nanotech, 4(4):265-70, 2009) that is capable of discriminating the four nucleoside 5'-monophosphate molecules with high accuracy. However, this mutant pore does not appear to have sensitivity for sequencing intact heteromeric ssDNA that passes through the pore.

Figure 3:
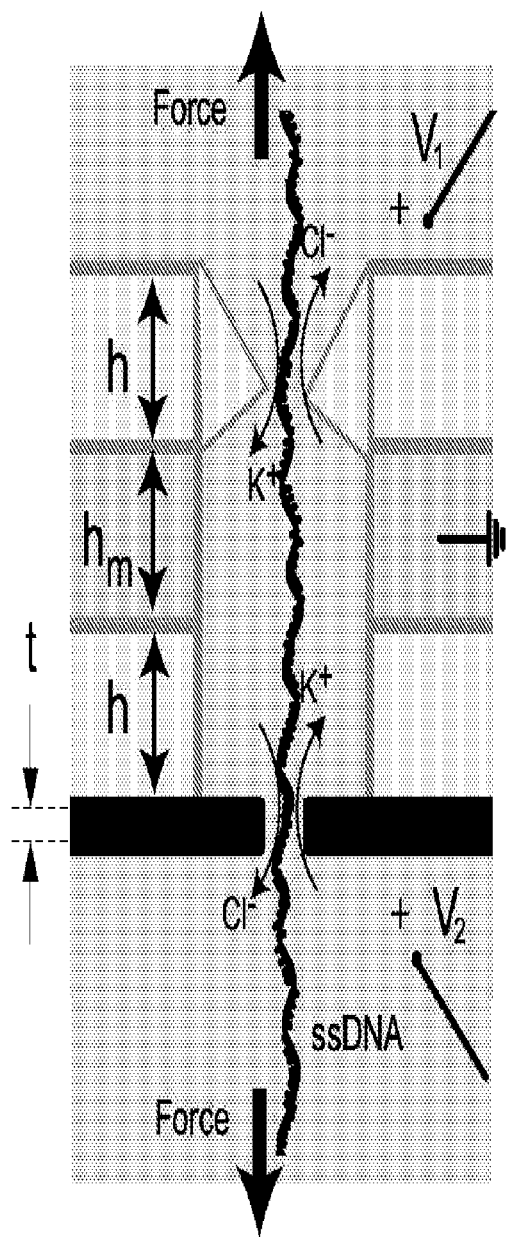
FIG. 3 illustrates that a DNA molecule captured in the dual-pore channel can be electrophoretically controlled by competing voltages, and ionic (KCl) current through the metallic membrane pore can be examined for single-nucleotide sensitivity. This figure also shows closure of the top nanopore (2-10 nm diameter) to provide a two-pore configuration that may improve control. Target chip parameter ranges include: $10 \leq h \leq 50$ nm, $50 \leq h_m \leq 100$ nm, $t=10$ nm, dual-pore channel diameter: 20-100 nm. Arrows show direction of voltage forces during electrophoretic control, with $|V_1|=|V_2|+\delta V$, and small $\delta V>0$ ($<0$) for tunable, net motion in the direction of chamber A (B).

Another exemplary biological pore is MspA, which has a funnel-like shape that focuses the sensitivity of the ionic current to the bottom of the channel. Moreover, achieving rate reduction of DNA through MspA and α-hemolysin can be achieved by using enzymes. As shown in FIG. 1 of (Manrao et al., Nature Biotechnology, 30:349-53, 2012), rate reduction of DNA through is achieved with the enzyme perched on the MspA nanopore. However, this results in non-deterministic sensing durations, repeated reads induced by backtracking, and an inability to sense homopolymeric regions. The mechanism of phi29 polymerase mediated DNA translocation was developed in (Cherf et al., Nat. Biotech., 30(4):344-8, 2012) on α-hemolysin and implemented on the more sensitive MspA nanopore (Manrao et al., Nature Biotechnology, 30:349-53, 2012). Step-wise rates of polymerization-catalyzed translocation are 2.5-40 nt/s, meeting the requirements for DNA rate reduction. However, while enzymes on biopores can reduce the rate of translocation, there is lack of control over the dwell time of each nucleotide, which will make blind tracking of repeats very difficult, and challenging to differentiate from long pauses on a single nucleotide read. In terms of sensitivity, as shown in FIG. 3 of (Manrao et al., Nature Biotechnology, 30:349-53, 2012), reading a repetitive DNA template can be achieved with phi29 on MspA. The FIG. 3a) shows an example trace for a DNA template composed of repeated CAT trinucleotides, with the exception of one CAG triplet in the middle of the sequence. The * represent "toggles" detected (by human analysis) as repeated transitions between two levels, which are intrinsic to the enzyme-based control method and incur read errors. The FIG. 3b) also shows Idealization of (3a), with mean currents of levels aligned with the known DNA sequence, and removing disparity of measured durations shown in (3a). Idealization shows a repeating pattern of three levels interrupted by the single dG substitution. Four levels are affected by the single dG with the largest deviations closest to the substitution, suggesting residual current is principally influenced by ~4 nucleotides. That the ionic current through MspA is influenced by ~4 nucleotides most proximal to the limiting aperture adds considerable complexity to identifying the sequence. While one would ideally build a library of distinct current amplitudes that map to each of the $4^4$=256 combinations, as suggested in the art, such a library will be difficult to achieve. The reason is that identifying step transitions in channel current recordings requires a signal-to-noise ratio (SNR) of at least 2 with half-amplitude methods (SNR 1.5 for Markov-based methods). With RMS noise of 0.5 pA at recording bandwidths, amplitudes shifts must be at least 1 pA to have the required SNR, resulting in only ~40 detectable levels within the amplitude range of 40 pA with MspA (or, at most 53 levels at SNR 1.5). Moreover, fewer than 40 levels will be observed since the range will not be uniformly utilized, and while further filtering could reduce noise to add amplitude discrimination it also results in missing more of the faster ssDNA motion transitions that are already present.

Presently, there is no nanopore for which ionic current sensing can provide single-nucleotide sensitivity for nucleic acid sequencing. Still, improvements to the sensitivity of biological pores and solid-state pores (graphene) are active and ongoing research fields. One issue is that ionic current sensing does not permit direct tracking of progress through homolymeric regions (base repeats), since there is no distinct signal-per-nucleotide of motion of homopolymeric ssDNA through the pore. Tracking repeats is essential, for example, since deletions and insertions of specific mononucleotide repeats (7, 9 nt) within human mitochondrial DNA have been implicated in several types of cancer (Sanchez-Cespedes, et al., *Cancer Research*, 61(19):7015-7019, 2001). While enzymes on biopores can reduce the rate of translocation, there is lack of control over the dwell time of each nucleotide. On the other hand, using a constant delivery rate with two-pore control, non-deterministic pauses are eliminated, and accurate estimation of repeat lengths can be made. Re-reading the repeat section many times can also improve the estimation errors and identify error bounds, and this can be done without having to reverse the polymerization chemistry caused by enzymes.

A recent study showed that, with a single nanopore, reduced rates cannot be achieved by merely reducing the voltage (Lu et al., *Biophysical Journal*, 101(1):70-9, 2011). Instead, as voltage is reduced, the rates of a single-stranded DNA (ssDNA) become more random (including backtracking), since Brownian motion becomes an increasing contributor to velocity fluctuations. The study also shows that high voltage force is required to suppress Brownian-motion induced velocity fluctuations that will otherwise confound sequencing measurements, even when using an idealized single-nucleotide-sensitive nanopore sensor.

The sequencing method provided in the present disclosure, based on a two-pore device, provides a ready solution to these problems and additional advantages over the existing methods. In concert with one or two pores that have sufficient sensitivity for sequencing, at high or low voltage, the two pore control solves the sequencing rate control problem of single nanopore implementations. Such pores can include biological pores housed in solid-state substrates, biological pores in membranes formed across solid-state substrates, or solid-state pores (for example, in graphene, silicon, or other substrates). In one aspect, an enzyme such as phi29 on a biological pore such as MspA can be used at one or both pores, with high voltages used to generate large signals for sequencing and a low differential voltage that generates a force on each enzyme that is sufficient to hold the enzymes in position atop each pore and permit polymerization-catalyzed DNA motion, but not large enough to stall or dissociate the enzymes. Such a configuration can improve the methods in Cherf et al., *Nat. Biotech.*, 30(4):344-8, 2012 and Manrao et al., *Nature Biotechnology*, 30:349-53, 2012, by significantly boosting the measurement signal, and permitting two pores to read one stand of DNA at the same time.

In addition, the method of the present disclosure can generate sufficiently high voltage at the pore to ensure detection sensitivity at the pore using ionic current sensing. It is plausible that high voltage would suppress Brownian motion enough to ensure constant rates through each pore, and configuration of the DNA outside each pore will affect the energetics of motion of DNA in either direction. Additionally, the voltage competition used in the method (FIG. 3) can be tuned so that the molecule spends sufficient time in the pore to allow analysis of the molecule. Still further, the present method is free of the need for enzymes, optics, or attachments to the DNA. Therefore, the method provides high signal-to-noise detection currents through the nanopore while regulating the molecule delivery rate, a capability that is not possible with single nanopore implementations.

The method can be used to identify the composition of monomers in a charged polymer. In one aspect, the monomer unit is a nucleotide when the polymer is a single stranded DNA or RNA. In another aspect, the monomer unit can be a nucleotide pair, when the polymer is double stranded.

In one aspect, the method can be used to identify a modification to the polymer, such as a molecule bound to a monomer, in particular when the bound molecule is charged. The bound molecule does not have to be charged, however, as even a neutral molecule can change the ionic current by virtue of its size.

In another aspect, the modification comprises the binding of a molecule to the polymer. For instance, for a DNA molecule, the bound molecule can be a DNA-binding protein, such as RecA, NF-κB and p53. In yet another aspect, the modification is a particle that binds to a particular monomer or fragment. For instance, quantum dots or fluorescent labels bound to a particular DNA site for the purpose of genotyping or DNA mapping can be detected by the device. Accordingly, the device of the present disclosure provides an inexpensive way for genotyping and DNA mapping as well, without limitation.

In one aspect, the polymer is attached to a solid support, such as a bead, at one end of the polymer.

Also provided, in one embodiment, is a method for determining the sequence of a polynucleotide, comprising: loading a sample comprising a polynucleotide in one of the first or second chamber of the device of any of the above embodiments, wherein the device is connected to a voltage-clamp or patch-clamp system for providing a first voltage between the first chamber and the middle layer, and a second voltage between the middle layer and the second chamber; (b) setting an initial first voltage and an initial second voltage so that the polynucleotide moves through the chambers, thereby locating the polymer across both the inlet and outlet; (c) adjusting the first voltage and the second voltage so that both voltages generate force to pull the polynucleotide away from the middle layer, wherein the two voltages are different in magnitude, under controlled conditions, so that the polynucleotide moves through the channel and both the inlet and the outlet in one direction and in a controlled manner; and (d) identifying each nucleotide of the polynucleotide that passes through the inlet or the outlet, when the nucleotide passes that inlet or outlet.

EXAMPLES

The present technology is further defined by reference to the following examples. It will be apparent to those skilled in the art that many modifications, both to devices and methods, may be practiced without departing from the scope of the current invention.

Example 1. Capture and Control of Individual dsDNA Molecules in Pores

This example shows that capture of DNA into each pore in a two-chamber dual-pore device is readily detected as shift in each independent ionic pore current measured.

This example demonstrates dual-pore capture using dsDNA with and without a bead attached to one end. Experiments with bead-tethered ssDNA can also be explored.

Upon capture and stalling of the DNA, the pore voltage nearest the bead can be reversed and increased until the competing force on the DNA draws it back toward the other chamber. The ionic current in either pore (inlet or outlet) can readily detect capture and exit of the DNA during the experiment.

When a bead is used, the bead has a proper size that prevents the bead from passing the channel. Methods that ensure a 1 to 1 bead-DNA ratio have been developed in the art. For example, monovalent streptavidin-coated Quantum dots (QDs; QD655, Invitrogen) conjugated to biotinylated DNA duplexes (or ssDNA) can provide beads in the 20-30 nm diameter range, with larger beads (30-100 nm) possible by using gold particles or latex. The influence of bead on hydrodynamics and charge, as it relates to capture rate, can be considered in designing the experiments.

Without beads, dsDNA passes through a pore at ~0.1 ms/kbp. DNA of lengths 500 bp and 4 kbp, and λ-phage dsDNA molecules (~48 kbp) can be used. DNA samples can be delivered from one chamber through the channel, using a common voltage polarity for each pore to promote capture from one chamber and passage through the channel into the other chamber. The large persistence length of dsDNA (one Kuhn length is 100 nm) ensures that the DNA segment inside each pore is likely fully extended and rod-like. Voltage and ionic concentration can be varied to identify adequate capture rates. Different buffered ionic concentrations can also be used in each chamber to enhance or alter capture rates, and conductance shift values that register the presence of DNA in each pore.

Using nanopore diameters 10 nm and larger minimizes the interaction (for example, friction and sticking) between dsDNA and the nanopore walls. For larger pores, although dsDNA can be captured in an unfolded and folded configurations, the single-file (unfolded) configuration is more likely at higher voltages, and with shorter (≤3 kbp) dsDNA. For an inter-pore distance of 500 nm or less, it is contemplated that the probability of dual-pore capture, following capture at the first pore (either inlet or outlet) is very high, for voltages of at least 200 mV in 1 M KCl (FIG. 3).

The radial distance within which voltage influence dominates thermal diffusion, and leads to capture with high likelihood, has been estimated to be at least 900 nm (larger than the inter-pore distance) for a range of pore sizes (6-15 nm diameter), voltages (120-500 mV), and with dsDNA at least 4 kbp in length (Gershow and Golovchenko, *Nature Nanotechnology*, 2:775-779, 2007). These findings support a high likelihood of prompt dual-pore capture of dsDNA, following single (first) pore capture of the dsDNA.

The capture and control of DNA through the two pores can benefit from active control hardware and real-time algorithms. The inventors have developed active control hardware/software for DNA control. See, for example, Gyarfas et al, *Biophys. J.*, 100:1509-16, 2011); Wilson et al., *ACS Nano.*, 3(4):995-1003, 2009; and Benner et al., *Nat. Nanotech.*, 2(11):718-24, 2007. A useful software is the LabVIEW software (Version 8, National Instruments, Austin, Tex.), implemented on an FPGA (field-programmable gate array) system (PCI-7831R, National Instruments)). The referenced FPGA can control up to 4 amplifiers simultaneously. Further, the Axon Digidata 1440A Data Acquisition System used to digitize and log data onto a PC has 16 input channels, enough to record voltage and current for up to 8 amplifiers in parallel. Other real-time operating system in concert with hardware/software for real-time control and measurement could also be used for controlling the amplifiers, and digitizing and logging the data.

The inventors have also developed a low-noise voltage-clamp amplifier termed the "Nanoclamp", (Kim et al., *IEEE Trans. On Biom. Circ. And Syst*. In press, May 2012; Kim et al., *Elec. Lette.*, 47(15):844-6, July, 2011; and Kim et al., *Proceedings of the IEEE International SoC Design Conference (ISOCC)*, November, 2010) to functionalize and optimize the use of one or more nanopores in small-footprint and multi-channel devices. Any other commercial bench-top voltage-clamp or patch-clamp amplifier, or integrated voltage-clamp or patch-clamp amplifier could be used for two pore control and measurement.

For a variety of solid-state pore materials and diameters, 0.1-10 kbp takes ~1 ms to translocate. With a FPGA-controlled amplifier, one can detect capture and initiate competing voltage control within 0.020 ms, much faster than the 1 ms total passage time of 1 kbp DNA; thus, triggering the control method before DNA escapes (with no bead attachment) also has high likelihood. As demonstration of control, the time to, and direction of, exit of the molecule from the pores can be demonstrated as a function of the magnitude of and difference between the competing voltages (FIG. 3). In single pore experiments, large fluctuations in the velocity of long WI kbp) dsDNA through the pore are experimentally observed, and these fluctuations are too large to be attributed to diffusional Brownian motion. In (Lu, et al., *Biophysical Journal*, 101(1):70-79, 2011), the dominant source of the net velocity fluctuations (that is, DNA length divided by total passage time) was modeled as being due to viscous drag induced by the voltage affecting portions of the DNA not yet in the pore, in addition to portion in the pore, where the voltage region of attraction extends. The model matched experimental data reasonably well. Notably, if the center of mass of the dsDNA is colinear with the pore upon capture, net velocity is faster, but if it is offset from the pore, net velocity is slower. When competing voltages are engaged in the two-pore device, dsDNA velocities will not be affected by this viscous-drag-induced perturbation, unless the voltage difference is sufficiently high. The reason is that, after dsDNA capture through both pores and competing voltage is engaged, the dsDNA between the pores will be fully extended and rod-like, and therefore cannot engage in creating structures near either interior pore entry. On the other hand, dsDNA structures on the exterior sides of the pores are constantly forced by each local pore voltage away from the middle channel, and are thus less likely to confound the pore entry kinetics. Such structure may affect the controlled delivery kinetics, and calibration experiments can be used to quantify this.

Force uncertainty induced by random transverse DNA motion is likely minimal. Additionally, the voltage force causes an electroosmotic flow (EOF) in the opposite direction of DNA motion, causing the DNA to move slower than it would in the absence of the induced counterion flow. Since different radial positions of the molecule can give rise to different EOF fields in the nanopore, one issue is whether the effective charge density and therefore the net driving force vary enough during fluctuations in DNA radial position to induce speed fluctuations. It is believed that the effective charge density of DNA in 1M KCl is stable for a distance of 1 nm or more between the pore wall and the DNA.

Additionally, SiN nanopores have a negative surface charge that intrinsically repels DNA. Thus, although the molecule will undergo radial position fluctuations, by using SiN pores with diameter greater than a few nanometers, it is likely that each constant voltage value will result in a constant effective force at each of the two pores, and thus a constant velocity in the direction of larger force when using two competing voltages in the two-pore setup. Treatment of other pore material surfaces can produce comparable effects to that of SiN.

Velocity uncertainty induced by random translational DNA motion that is caused by Brownian motion may be reduced by increasing the competing voltages. Experiments can be carried out to determine whether such reduction will occur. A single-nanopore study (Lu, et al., *Biophysical Journal*, 101(1):70-79, 2011) supports that increasing the competing forces can reduce uncertainty caused by Brownian motion. The study analyzed the velocity fluctuations caused by Brownian motion, which occur on fast (nanosecond) time scales, and the sequencing errors that result from such fluctuations. Assuming a hypothetical and idealized single-nucleotide sensor (noise-free detection at >22 MHz bandwidth), Brownian motion alone results in 75% read error. The relevant parameter for predicting the error is $k_B T/F*(0.34$ nm$)$, which is the ratio of thermal energy to the work done to translocate the DNA the distance a between nucleotides (0.34 nm). In the ratio, force $F=V\lambda$, is the voltage V driving DNA with charge density $\lambda$ (0.2 e$^-$/bp for dsDNA). For the present control method, increasing the voltage 50× results in 5% read error, with higher voltage further improving errors. With a single pore, however, since mean velocity $\bar{v}$ is $F*d/(k_B T)$ with diffusion constant d, DNA speed also increases with F, placing even more unrealistic demands on the sequencing bandwidth.

To maintain the 22 MHz bandwidth, a 50× increase in force with a single nanopore would have to be paired with a 50× increase in solution viscosity to maintain the same $\bar{v}$. Practically, however, 22 MHz bandwidth is already much higher than any experimental nanopore platform has demonstrated, or promises to demonstrate, for single-nucleotide sequencing. Moreover, increasing viscosity can slow DNA only up to 10× (Fologea, et al., *Nano Lett.*, 5(9):1734-7, 2005) with single nanopores. Using the two-pore platform, each voltage can be kept sufficiently high, and this may suppress fluctuations caused by Brownian motion, while the differential voltage that determines the net DNA speed can be adjusted to ensure control rates are within actual sequencing bandwidths (nominally 1 kHz). An alternative method of suppressing Brownian motion induced velocity fluctuations is to use feedback control. In one aspect, with 10 kHz bandwidth of the second pore current feedback to actuation of the first pore voltage at 10 kHz bandwidth, Brownian motion can be compensated to control detectable features on the DNA to remain in and near the second pore at these kHz closed-loop bandwidths. This capability is a one-dimensional analogue to the anti-Brownian electrokinetic (ABEL) trap that suppressed Brownian motion in two spatial dimensions and works by optical forcing of beads attached to molecules at Hz closed-loop bandwidths (Wang and Moerner, *ACS Nano*, 5:5792-9, 2011). There is precedent for creating stiction force between DNA and (positively charged) nanopore walls. For instance, Bashir and coworkers (Venkatesan et al., *Adv. Mater.*, 20(8):1266-75, 2010; Venkatesan et al., *Adv. Mater.*, 21:2771-6, 2009) reported the potential for $Al_2O_3$ pores to significantly reduce translocation rates due to their unique ability to form positively charged crystal domains from sputtering—the negatively charged phosphate backbone of DNA, while traversing an $Al_2O_3$ pore, interacts with the positive surface, slowing its movement. Recent work by Dekker and coworkers (Kowalczyk et al., *Nano. Lett.*, 12:1038-44, 2012) showed that LiCl slowed DNA rates by 10×, compared to the commonly used KCl ionic solution, provided a method that any nanopore setup could benefit from.

Example 2. Detection and Localization of RecA Filaments Bound to DNA

This example shows that the two-chamber dual-pore device can be used to map the binding of a DNA-binding protein to dsDNA, and for proteins that do or do not bind to specific sequences.

As demonstrated in Example 1, DNA samples can be captured from one chamber. RecA protein catalyses an ATP-dependent DNA strand-exchange reaction that pairs broken DNA with complementary regions of undamaged DNA. Using a poorly hydrolyzable ATP analogue ATP γS, RecA filaments bound to dsDNA are very stable in high salt (for example, 1M KCl) when first assembled in physiological salt. As an alternative to ATPγS, which is slowly hydrolyzed, this example can also use ADP-AlF4 (aluminum tetrafluoride), which does not turnover at all, and causes RecA to bind more tightly to the DNA.

Detection of RecA filaments bound to λ-DNA through 20-30 nm nanopores has been demonstrated (Kowalczyk et al., *Nano Lett.*, 10(1):324-8, 2010; Smeets et al., *Nano Lett.*, 9(9):3089-95, 2009; and Hall et al. *Nano Lett.*, 9(12):4441-5, 2009], but filaments <20 bp (6 or fewer RecA proteins) in length cannot be resolved using a single nanopore, due to the coupling between translocation rate and measurement SNR.

Initial experiments of this example use bead-bound and unbound λ-DNA that has been exposed to varying concentrations of RecA, to generate DNA that is nearly uncoated, partially coated, and fully coated. Real-time monitoring of each pore current can be used to gauge progress of the controlled delivery, and will be correlated for location mapping of the filaments. Repeated measurements of each DNA will improve accuracy of RecA mapping.

The added charge and bulk, and stability in high salt, when RecA is bound to DNA make it an ideal candidate to attempt detection and location mapping during controlled delivery with the proposed instrument.

Control of RecA-bound DNA can also be attempted without a bead attached to arrest translocation. As with dsDNA experiments in Example 1, active voltage control can be used to promptly initiate competing voltage control before the DNA exits the nanopores. As charged species that bind to DNA affect the mobility of DNA in an electric field, by altering the net charge and stiffness of the DNA, motion control tuning experiments can examine the influence of RecA binding to dsDNA on the force balance used to control the motion of the dsDNA.

This example can demonstrate that the shortest observed filament lengths, at low RecA concentrations, can be measured at high SNR and at sufficiently slow and controlled rates, so that any RecA protein bound in isolation can be detected if present.

The two-pore device therefore provides a completely new single-molecule instrument for basic research, as one could examine the capability to detect binding of additional proteins to the RecA-DNA filament, which would increase the filament width and thus be detected by a decrease in observed current. For example, proteins that bind to the RecA-DNA filament include LexA and bacteriophage lambda repressors, which use RecA to sense the status of the cell and switch on or off downstream regulatory events.

Calibration experiments would involve detecting proteins that bind to specific sequences (locations) on the DNA, so that protein-induced shifts in the current would then permit estimation of the speed and rate control performance of the DNA through the pores. Example proteins that bind to specific sites on dsDNA include Lac repressor (binds to a 21 bp segment), phage lambda repressor (which has multiple operator sites on λ-DNA), and other proteins.

Example 3. Detection and Localization of a Double-Stranded Segment within a Singled-Stranded DNA This example demonstrates the production of up to 10 kb ssDNA with doubled-stranded segments of varying lengths.

In a first step, 10 kbp dsDNA can be created by long range PCR. One end of the strand is biotinylated for bead attachment, and the strands are separated by chemical denaturing. The unbeaded 10 kb ssDNA then serves as the measured strand in two-chamber dual-pore experiments. Complementary single-stranded segments with desired sizes can be created by PCR followed by bead capturing and strand separation.

ssDNA segments of varying lengths and at multiple sites within the measured 10 kb ssDNA can be used, starting with a set of 100 nt segments. Ionic current through a single solid-state pore was used to differentiate dsDNA from ssDNA homopolymers, and purine and pyrimidine homopolymers in (Skinner et al., *Nano Lett.*, 9(8):2953-60, January 2009). Thus, likelihood of differentiating single from double stranded segments in DNA is high at sufficiently high voltage using the two-pore device. Mapping ssDNA vs. dsDNA segments enables nanopore sequencing using the hybridization-assisted method (though this method as proposed relies on a costly hybridization-assisted process), and can be used reveal both location and identity of target DNA sequences over long distances (targeted sequencing). One can also explore the use of Single Strand DNA Binding (SSB) proteins, as beads that will further amplify the ssDNA vs. dsDNA differences in ionic current by binding to the ssDNA and creating a larger impedance than dsDNA.

Example 4. Capture and Control of Long ssDNA and Localization of RecA

This example demonstrates the capture and control of a long ssDNA and the detection and localization of a RecA filament bound to the ssDNA. Additionally, it shows that the two-pore device can detect purine vs. pyrimidine homopolymeric segments within the ssDNA.

Stochastic detangling of 7 kb ssDNA through a 10 nm pore in a 20 nm SiN membrane can be carried out as shown in Stefan et al., *Nano Lett.*, 10:1414-20, 2010. While the single-nanopore method in Stefan et al. 2010 unravels the ssDNA by the mechanical contact force between the tangled ssDNA and the pore/membrane surface, it is contemplated that the dual-pore competing voltage setup can electrophoretically force ssDNA to detangle near and in between the pores at sufficiently high competing voltages, by the action of each voltage force on the DNA backbone nearest each pore.

Detangling and subsequently precision control of the rate of ssDNA through the two pore setup is important for eventual sequencing of long ssDNA molecules. At sufficiently high voltage (~400 mV), it is possible to discriminate purine and pyrimidine homopolymeric segments within ssDNA (Skinner et al., *Nano Lett.*, 9(8):2953-60, January 2009), which is valuable for diagnostic applications and possibly cancer research.

This example also explores the use of RecA, or perhaps other Single Strand DNA Binding (SSB) proteins, as detectable "speed-bumps" that are differentiable from the ssDNA ionic current by binding to the ssDNA and creating a larger impedance. These speed bumps will allow direct quantification of the controlled ssDNA speeds that are possible, which in turn will demonstrate that the required 1 ms/nt is achievable. Since RecA is not required to bind to specific trinucleotide sequence sites, but binds preferentially to TGG-repeating sequences and also tends to bind where RecA filaments are already formed, calibration experiments will require the use of other ssDNA binding molecules that do bind to specific known sequence locations. Having known binding sites that are detectable as they pass through each pore is required to determine the speed of the molecule as a function of the competing voltage values. A non-limiting example is to use duplex strands (or bead-tethered duplex strands) that hybridize to one or more known sites, from which the shifts in current could be used to detect passage of each duplex through each pore, and then estimate the passing strand speed for the chosen voltage values. Subsequently, RecA filaments can be formed and detected on such molecules, keeping the duplex feature(s) as benchmark detection points relative to which RecA filaments can be detected and their position inferred.

Methods for determining genetic haplotypes and DNA mapping by incorporating fluorescent labels into dsDNA (Xiao, et al., U.S. Pat. No. 7,771,944 B2, 2010) can also use the two pore device, since the bead labels (for example, quantum dots, or any fluorescent label) is bulkier and will produce shifts in the current just as binding proteins on dsDNA would. Moreover, the two-pore method is simpler and much less expensive than using high resolution imaging methods (that is, total internal reflection fluorescence microscopy) to detect and map the label positions. It is also noted that any velocity fluctuations caused by Brownian motion during controlled delivery are much less deleterious for detecting larger features (proteins, duplex segments, bead attachments) than for detecting smaller features.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A system comprising:
   a channel through and defined by a plurality of layers surrounding the channel, the channel connecting a first chamber and a second chamber separated by the plurality of layers,
   the plurality of layers comprising:
      a first layer, and
      a conductive layer coupled to the first layer and surrounding the channel,
   the channel comprising an inlet and an outlet defined by the plurality of layers, the inlet and the outlet being between 10 nm and 1000 nm apart from each other, the conductive layer coupled to a power supply,
wherein the system further comprises at least one sensor capable of detecting a polymer component during movement of the polymer component into the inlet, and wherein the sensor measures an ionic current through the inlet.

2. The system of claim 1, wherein at least one of the inlet and the outlet defines an opening that is from 0.5 nm to 100 nm in diameter.

3. The system of claim 1, wherein at least one of the inlet and the outlet is defined by a layer having a thickness of from 0.1 nm to 100 nm.

4. The system of claim 1, further comprising a first electrode coupled to the conductive layer.

5. The system of claim 4, further comprising a second electrode positioned within the first chamber.

6. The system of claim 1, wherein the conductive layer is composed of at least one of gold, platinum, aluminum, and chrome.

7. The system of claim 1, wherein the power supply is configured to provide a first voltage $V_1$ between the first chamber and the conductive layer, and a second voltage $V_2$ between the conductive layer and the second chamber.

8. The system of claim 7, wherein the first voltage $V_1$ and the second voltage $V_2$ are independently adjustable.

9. The system of claim 1, wherein the second chamber is coupled to a fluid channel in fluid communication with a reservoir of the system.

10. The system of claim 1, wherein the inlet is coaxial with the outlet.

11. The system of claim 1, wherein the polymer component comprises a nucleotide, and wherein the system is configured to translocate the nucleotide from the inlet to the outlet with application of a voltage differential across the first chamber and the second chamber by the power supply.

12. The system of claim 1, wherein the polymer component comprises a double stranded DNA component.

13. The system of claim 1, wherein the polymer component comprises a single stranded nucleic acid component.

14. A method for controlling movement of a charged polymer through a channel, the method comprising:
receiving a sample comprising a charged polymer into one of a first chamber and a second chamber of a system, the system comprising:
a channel through and defined by a plurality of layers surrounding the channel, the channel fluidly coupling the first chamber and the second chamber,
the plurality of layers comprising:
a first layer, and
a conductive layer coupled to the first layer,
wherein the channel comprises an inlet and an outlet defined by the plurality of layers, and
wherein the inlet and the outlet are between 10 nm and 1000 nm apart from each other; and
applying a differential voltage across the first chamber and the second chamber,
wherein applying the differential voltage comprises setting a first voltage $V_1$ at the first chamber and a second voltage $V_2$ at the second chamber, and
wherein the first voltage $V_1$ is different in magnitude from the second voltage $V_2$, thereby controllably driving the charged polymer through the channel in one direction.

15. The method of claim 14, further comprising adjusting the first voltage $V_1$ and the second voltage $V_2$ such that the first voltage $V_1$ and the second voltage $V_2$ generate forces to pull the charged polymer away from the conductive layer.

16. The method of claim 14, wherein the first voltage and second voltage are 10 to 10,000 times greater in magnitude than the difference between the first voltage $V_1$ and the second voltage $V_2$.

17. The method of claim 14, wherein the charged polymer comprises one of: a double stranded DNA component and a single stranded nucleic acid component.

* * * * *